(12) United States Patent
Du et al.

(10) Patent No.: US 7,809,103 B2
(45) Date of Patent: Oct. 5, 2010

(54) METHOD FOR DETECTING THE PRESENCE OF HIGH ATOMIC NUMBER ELEMENTS

(75) Inventors: Yanfeng Du, Rexford, NY (US); Forrest Frank Hopkins, Cohoes, NY (US); Joseph Bendahan, San Jose, CA (US)

(73) Assignee: General Electric Company, Niskayuna, NY (US)

( * ) Notice: Subject to any disclaimer, the term of this patent is extended or adjusted under 35 U.S.C. 154(b) by 796 days.

(21) Appl. No.: 11/756,027

(22) Filed: May 31, 2007

(65) Prior Publication Data

US 2010/0166142 A1 Jul. 1, 2010

(51) Int. Cl.
*G01N 23/087* (2006.01)
(52) U.S. Cl. .......................................... 378/53; 378/57

(58) Field of Classification Search ................... 378/51, 378/53, 54, 55, 56, 57
See application file for complete search history.

(56) References Cited

U.S. PATENT DOCUMENTS

| 7,308,077 B2 * | 12/2007 | Bijjani et al. | 378/57 |
| 2005/0276376 A1 * | 12/2005 | Eilbert | 378/57 |
| 2009/0086907 A1 * | 4/2009 | Smith | 378/57 |

* cited by examiner

*Primary Examiner*—Hoon Song
(74) *Attorney, Agent, or Firm*—Joseph J. Christian (57) ABSTRACT

Disclosed herein is a method for detecting high atomic number elements in an article by using radiation having two different energies. The detecting of high atomic number elements can be accomplished by using an algorithm, curve fitting or using a data table. Disclosed herein too is a radiation system that uses the aforementioned method for detecting high atomic number elements.

13 Claims, 4 Drawing Sheets

Remove steel

FIG. 4

METHOD FOR DETECTING THE PRESENCE OF HIGH ATOMIC NUMBER ELEMENTS

BACKGROUND

This disclosure relates to a method for the detection of the presence of high atomic number elements. This disclosure also relates to a method for detecting the atomic number of hitherto unknown elements in an article.

The modern global economy relies heavily on intermodal shipping containers for rapid, efficient transport of ocean-going cargo. However, the possibility of concealing weapons of mass destruction (WMDs) and radiological dispersal devices (RDDs) in these containers represents a potential interruption to the free flow of commerce. Materials of concern such as uranium and plutonium that can be used to make nuclear weapons are characterized by having a high atomic number (high-Z). Similarly, radiological sources can be shielded employing high-Z materials to prevent these from being detected. Current x-ray inspection systems are not capable of detecting such materials and distinguishing them from common materials with a low false alarm rate.

Currently, when a radiographic image of an article is made, the intensity of various elements seen in the radiographic image represents the product of the materials linear x-ray attenuation coefficients and the path lengths at each pixel. A given product can be produced by different combinations of attenuation coefficients and path lengths. For example, a section of an article that has a thickness 'x' and is made from a material that has a low atomic number can produce the same intensity in a radiographic image as another section of the same article that has a thickness less than x but is made from a material that has a higher atomic number.

Figure 1:
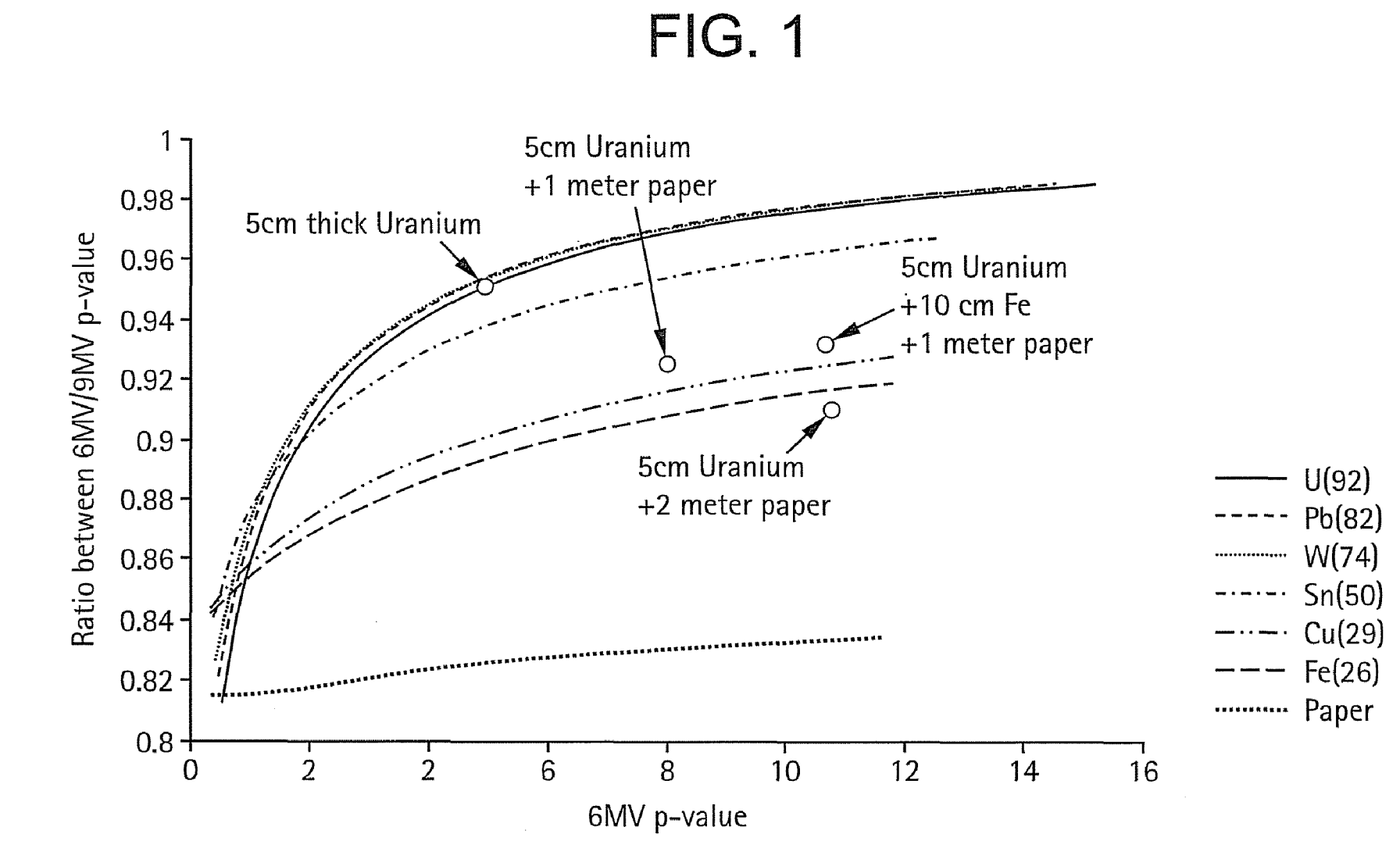
FIG. 1 is a graphical representation depicting the x-ray attenuation dependence at 6 megavolts (MV) and 9 MV for different materials.

FIG. 1 is a graphical representation of the radiographic imaging of a multi-layered article produced with a high energy X-ray source called a linac for which the X-ray energies are determined by the voltage setting of the linac. A convenient term for indicating the total attenuation in a given object or objects is called the p-value, defined as shown in Equation (I) below:

$$P = -\log\left(\frac{I_{object}}{I_{air}}\right) \quad (I)$$

where $I_{object}$ is the measured energy with the article at a given pixel or a given collection of pixels, while $I_{air}$ is the measured energy of the radiation without the article measured at the at the same pixel or given collection of pixels.

In FIG. 1, the ratio of the p-values at two different X-ray source voltage settings, 6 MV and 91 MV, is shown as a function of the p-value for the lower energy setting. As can be seen in the FIG. 1, when a sample comprising a 5 centimeter thick uranium slab wrapped in paper having a thickness of 2 meters is radiographically imaged using an xray source, the p-value is similar to the p-value of a sample comprising a 5 centimeter thick uranium slab and a 10 centimeter thick iron slab wrapped in paper having a thickness of 1 meter.

Thus, the simple radiographic imaging of the p-values for composite samples comprising multiple layers of different materials does not produce results that can facilitate a distinction or identification of different types of materials. It is therefore desirable to have a radiography device and a method that can distinguish between materials having different atomic numbers, when these materials are present individually or when they are in the presence of other materials.

SUMMARY

Disclosed herein is a method for inspecting an article comprising a plurality of elements, wherein one element is selected as a background element, the method comprising irradiating the article with radiation comprising a first energy and a second energy; receiving data that corresponds to the first energy and the second energy; processing the data to generate a first data set and a second data set; wherein the first data set corresponds to the first energy and wherein the second data set corresponds to the second energy; obtaining an attenuation ratio for the background element present in the article; the attenuation ratio for the background element being an attenuation in energy produced by the background element at the first energy to an attenuation in energy produced by the background element at the second energy; subtracting the attenuation ratio for the background element at the second energy from a product of the attenuation ratio for the background element with the first energy data set to form a filtered data set; identifying a region of interest in the filtered data set; and calculating an effective atomic number from the filtered data set for elements that have an atomic number greater than the background element in the region of interest.

Disclosed herein too is a radiography system for implementing the aforementioned method.

DETAILED DESCRIPTION

As used herein, the singular forms "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Also as used herein, the phrase "generating an image" is not intended to exclude embodiments of the disclosure in which data representing an image is generated but a viewable image is not. However, many embodiments generate (or are configured to generate) at least one viewable image. It is also to be understood that a data set can be used in lieu of generating an image.

As used herein, the phrases "multi-element article" or "articles having a number of elements" or the like, encompass articles having two or more base elements (including articles intended to have-two or more base elements), articles comprising a single base element with another element or combination of elements located in the article (such as an aluminum honeycomb structure with lead located within the structure), and articles having one or more base elements with one or more of the base elements at least partially transformed, for example by aging or exposure (such as a metallic structure with corrosion).

Disclosed herein is a method for the detection of the atomic number of a plurality of different elements contained in an article, wherein each of the elements have a different atomic number. The method also permits the detection of the atomic number of a plurality of different elements contained in an article, when the elements are dispersed randomly or arranged in a multilayer fashion. More specifically, the method can be used to detect the atomic number of elements that can be used to make nuclear bombs or shield radiation.

In one embodiment, a method for inspecting an article comprising a plurality of elements comprises scanning or irradiating the article with radiation having a plurality of energies. In an exemplary embodiment, a method for inspecting an article comprising a plurality of elements comprises scanning or irradiating the article with energy having two or more different energies. An exemplary article that can contain different elements is a cargo container. Cargo containers that are shipped by road, rail, air or water can be inspected using the method described herein to detect the presence of elements having a high atomic number. This method can also be used in medical imaging to detect the presence of high atomic number elements in living beings.

The term radiation with "different energies" can be construed to mean radiation "that has different energy distributions". In an exemplary embodiment, the method comprises irradiating the article with radiation having a first energy distribution and a second energy distribution. The first energy distribution is not equal to the second energy distribution. In other words the mean of the first energy distribution is different from the mean of the second energy distribution. This also can be construed as different types of radiation, where the first energy refers to gamma rays and the second energy refers to neutrons, for example.

While a linear accelerator may be used to accelerate electrons to generate x-rays, it will be appreciated that the scope of the embodiment is not so limited, and that detection systems that use other forms of radiation, such as Coolidge x-ray sources, protons impinging on one or more target materials to generate gamma ray radiation, and deuterons impinging on deuterium, for example, to generate neutron radiation may also be used.

In an exemplary embodiment, radiation comprising the first energy is generally used prior to the radiation comprising the second energy. Radiation comprising the first energy can be used simultaneously along with the radiation comprising the second energy so long as the effects of the respective irradiations can be discriminated from one another.

Upon being subject to irradiation having a first energy and a second energy, the article interacts with the irradiation to produce a data set or an image. As noted above, the data set (obtained by the interaction of the radiation with the article) can be converted into an image. A data set (i.e., a collection of data points) is collected at each energy that the article is irradiated with.

A data point represents the measured intensity (as a result of the interaction between the article and the radiation) at each pixel and represents the energy attenuation line integral between that detector pixel and the energy source. The image intensity at each detector pixel contains an energy contribution from all relevant elements contained in the article that interact with the radiation (e.g., that scatter the radiation or facilitate its transmission). In one embodiment, an exemplary energy source for providing the first energy and the second energy is an x-ray source that can irradiate the article with different energies.

Thus, a first data set (or a corresponding image) is collected at the first energy while a second data set (or a corresponding image) is collected at the second energy. Following the collection of the respective data sets, the total attenuation at each respective energy can be calculated. In one embodiment, the ratio (i.e., the attenuation ratio) of the total attenuation at the first energy to the total attenuation at the second energy is measured. As will be detailed below, this attenuation ratio R is dependent upon the atomic number of elements present in the article.

In an exemplary embodiment, the total attenuation in the form of p-values may be measured at a given detector pixel or a given collection of detector pixels where the first and second data sets are collected. The p-value for each pixel includes the contributions from multiple overlapping elements in the article.

The ratio "R" of the data set at the first energy to the data set at the second energy (at a given detector pixel) for each element in the article has a unique dependence upon the p-value of the data at the first energy or the p-value of the data at the second energy. The ratio R is also called the p-value ratio and has a unique dependence upon the atomic number of a particular element present in the article.

The p-value ratio R for a given element in the article is defined as shown in Equation (II) below:

$$R = \frac{P_{low}}{P_{high}} = a_{z_0} + a_{z_1}.P_{low} + a_{z_2}.P_{low}^2 + \ldots \quad (II)$$

where $P_{low}$ is the p-value at the lower energy of the first energy or the second energy; $P_{high}$ is the p-value at the higher of the first energy or the second energy, and where the polynomial coefficients $a_{z0}$, $a_{z1}$ and $a_{z2}$ are dependent upon the atomic number Z.

As a result of the unique dependence of the ratio R for a given element on the p-value, the contribution from a given element can be removed (subtracted) from a data set or from the image. It is generally desirable to know the identity of the element whose contributions to the data set are to be removed from the data set. The contribution from the known element is termed the background. In order to remove the contribution of a particular element from the article, it is desirable to know its atomic number.

In one embodiment, removal of the background can comprise subtracting the attenuation ratio for the background element at the second energy from a product of the attenuation ratio for the background element with the first energy data set to form a filtered data set.

By removing the background from each of the data sets (or from the respective images), the contributions to the signal (p-value) at a given pixel from elements (in the article) having a lower atomic number than that of the background become negative contributions, while the contributions from elements (in the article) having a higher atomic number than that of the background become positive contributions. The materials that form the background can therefore be used as a filter to determine the atomic number of other hitherto unknown elements present in the article. Since a large portion of materials contained in articles such as cargo containers are not high atomic number elements, the removal of the background can be used as a method for detecting the presence of other high atomic number elements present in the container.

For example, if an article containing the element iron and other unknown elements is subjected to irradiation at a first energy and a second energy, the data set for iron can be removed from the data set at the first energy and/or the data set at the second energy for the article. As noted above, if an image of the article is obtained in lieu of a data set, then the image due to iron is removed. Since there is a unique dependence of the ratio R for a given element on the p-value and since the ratio R is higher for higher atomic number elements than for lower atomic number elements, the removal of the data set for iron gives rise to a new data set where all of the contribution from iron to the data set is reduced to zero, while the contributions from elements (in the article) having a lower atomic number than iron are negative contributions, while the contributions from elements (in the article) having a higher atomic number than iron are positive contributions.

Once the contribution from the background is removed from the data set, regions of the article having high atomic numbers show up as peaks in the filtered data set. If the filtered data set is alternatively represented by an image, the regions having higher atomic numbers than the element whose contributions were used as the background, show up as high relative opacity, or as whiter spots in a grayscale image. A region that appears as a peak in the filtered data set or as a white spot in a corresponding grayscale image can then be analyzed for its atomic number.

In one embodiment, in one method of analyzing the filtered data set or a corresponding image for its atomic number, a mathematical equation can be employed to determine the atomic number Z of the other elements present in the article. In another embodiment, if some of the other elements present in the article are known, then their contributions can also be estimated, following which a mathematical equation can be employed to determine the atomic number Z of the remaining elements present in the article. In yet another embodiment, curve fitting can be used to estimate the atomic number Z of the remaining elements present in the article. In yet another embodiment, if some of the other elements present in the article are known, then their contributions can also be estimated, following which curve fitting can be used to estimate the atomic number Z of the remaining elements present in the article. In yet another embodiment, a data table can be used to estimate the atomic number Z of the remaining elements present in the article.

Since the p-value ratio R has a unique dependence upon the atomic number Z of an element present in the article, a mathematical equation can be developed to link the atomic number Z of the element to the ratio R. In an exemplary embodiment, the mathematical equation can be a polynomial equation or a spline function. In one embodiment, the mathematical equation can be represented by the Equation (III)

$$Z = f(\text{filter}(R)) \quad \text{(III)}$$

As noted above, the ratio R is dependent upon $I_{object}$, which is dependent upon the thickness of the element that constitutes the background. The material thickness however, can be related to the p-value of the lower of the first energy or the second energy by a polynomial equation, an example of which is shown in the Equation (IV)

$$d = c_{z0} + c_{z1} \cdot P_{low} + c_{z2} \cdot P_{low}^2 \quad \text{(IV)}$$

where the polynomial coefficients $c_{z0}$, $c_{z1}$, $c_{z2}$ and the like are dependent upon the atomic numbers of the unknown elements present in the article.

Similarly, the atomic number Z can be related to the ratio R by a polynomial equation as shown in the Equation (V) below:

$$Z = b_{f0} + b_{f1} \cdot R + b_{f2} \cdot R^2 + \quad \text{(V)}$$

where the p-value ratio R is defined as shown in the Equation (II) and where the polynomial coefficients $b_{f0}$, $b_{f1}$, $b_{f2}$ and the like are dependent upon the element that constitutes the background and that is used as the filter.

By solving the Equations (N) and (V) above, the effective material thickness and the corresponding atomic number for various unknown elements present in the article can be determined. In an exemplary embodiment, an algorithm that can then solve Equations (IV) and (V) can be executed by a computational device in order to determine the effective material thickness and the corresponding atomic number.

It is to be noted that several known elements in the article can sequentially or simultaneously be used as the background and can be used for filtering the data set. In other words, a first known element can be used as a background and its contribution reduced to zero. A first region of interest analysis as described in the Equations (III), (N) or (V) can then be performed to determine the atomic number of unknown elements. Following this, if desired, a second known element can be used as the background and its contribution reduced to zero. A second region of interest analysis as described in the Equations (III), (N) or (V) can then be performed to determine the atomic number of unknown elements. In one embodiment, the second region of interest analysis can be performed as a quality check on the determinations made in the first region of interest analysis. In another embodiment, the second region of interest analysis can be performed to make determinations of the atomic numbers of elements that are not made in the first region of interest analysis.

In one embodiment, the method may be used for dynamically quantifying the constituents of the article based on the material characterization images, wherein the step of dynamically quantifying the constituents comprises determining an amount of one of the constituents relative to another of the constituents. Since the thickness each of the unknown elements can be obtained from the Equation (IV) and since the atomic number of the same element can be obtained from the Equation (V), it is possible to determine an approximate quantity of one unknown element relative to another unknown element present in the article. Thus the composition of the article can be mapped out.

Figure 2:
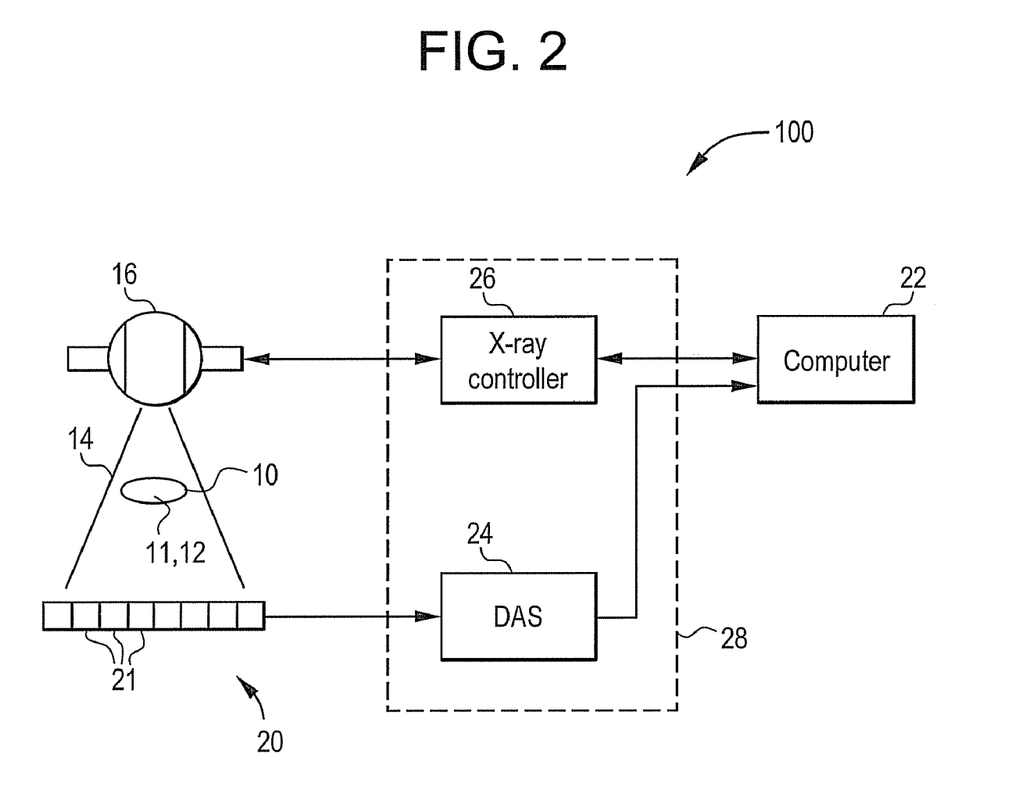
FIG. 2 schematically depicts one embodiment of a radiography system that can be used to determine the atomic number of hitherto unknown elements in an article.

A device or a radiography system can be used to implement the method described above. FIG. 2 depicts an exemplary radiography system 100 that can be employed to determine the atomic number Z of hitherto unknown elements in an article. In one embodiment, the radiography system 100 comprises at least one radiation source 16 configured to alternatively irradiate an article 10 with radiation 14 characterized by at least two different energies, where the article 10 has a number of elements 11, 12. The radiography system 100 further includes at least one radiation detector 20 configured to receive radiation 14 passing through article 10, and a computer 22 operationally coupled to the radiation detector 20. Computer 22 is configured to perform the following operations: receive data corresponding to each of the energy spectra for a scan of the article 10, process the data to generate a data set, remove the background and solve the mathematical equations to generate a number of material characterization images (not shown) in substantially real time.

The system can use other source/detector configurations as well. For example, a geometry system different from that of FIG. 2 may be employed, where there is an area source or an array of sources, and a single or reduced-size detector. In another embodiment, a number of sources may be employed, for example two x-ray tubes, operating at different energies, and are switched by gridding or shuttering.

As used herein, the phrase "substantially real time" refers to material imaging processes where the material characterization images are generated at up to 30 frames per second. In another embodiment, radiography techniques that collect and store information about the article and finally generate an image at a later time based on the gathered information can also be employed. Combinations of the aforementioned systems may also be used.

In one embodiment, by generating the multi-energy data set to produce the material characterization images in substantially real time, the inspection method can be used as a screening process with inspection of a relatively large area occurring in a short time frame. For example, the article 10 can first be inspected at a relatively short exposure. If the constituent of interest, for example a high atomic number element, is detected, longer exposure images can then be taken of the particular article 10 or portion of the article 10 (for example, a portion of an aircraft fuselage, a carriage or compartment of a locomotive or a semi-trailer truck, a section of a ship). Generating the material characterization images in substantially real time is useful for the application of this inspection method as a screening process. Similarly, the method can be used in a screening fashion to select the optimal source to detector distances (SDD), viewing angle, region of interest, and exposure, among others. As a result the method provides an improved tool for inspecting complex articles.

With reference now again to the FIG. 2, the computer 22 is also operationally coupled to the radiation source 16. Radiation source 16 projects a beam of x-rays 14 (radiation) towards the radiation detector 20 on the other side of the article 10. Exemplary radiation sources 16 include x-ray sources and gamma ray sources. Although many of the embodiments described herein depict x-rays as an exemplary type of radiation for radiographic imaging, it will be appreciated that the other sources of radiation or energy can also be used. Examples of other types of radiation or energy are electron beams, gamma rays, high-frequency sound waves, magnetic fields, neutrons, charged particles, or the like, or a combination comprising at least one of the foregoing.

The operation of radiation source 16 is governed by a control mechanism 28 of the radiography system 100. Control mechanism 28 includes an x-ray controller 26 that provides power and timing signals to radiation source 16. X-ray controller 26 is configured to receive control signals and/or information from the computer 22.

Radiation detector 20 includes at least one detector row (not shown), which, as indicated in the FIG. 2, includes a number of detector elements 21 (or pixels), which together sense the projected x-rays that pass through article 10. Each detector element 21 produces an electrical signal that represents the intensity of an impinging radiation beam and hence can be used to estimate the attenuation of the beam as it passes through article 10. In one embodiment, the radiation detector 20 includes a number of detector rows arranged in parallel to form a two-dimensional array of detector elements 21. Exemplary radiation detectors 20 include digital x-ray detectors, such as charge integration detectors, examples of which are included in General Electric Company's Revolution® digital x-ray detectors. In one embodiment, the radiation detector 20 is an energy discriminating detector. In addition, although digital x-ray detectors are generally rigid, the radiation detector 20 may also be flexibly configured to conform to the article 10. Further, although detector 20 is shown as straight, it may also be curved.

For the exemplary embodiment shown in FIG. 2, the radiography system 100 also includes a data acquisition system (DAS) 24 configured to receive data from radiation detector 20. More particularly, DAS 24 samples analog data from detector elements 21 and converts the data to digital signals for subsequent processing.

In one embodiment, the computer 22 includes a device, for example, a floppy disk drive, CD-ROM drive, DVD drive, magnetic optical disk (MOD) device (not shown), or any other digital device including a network connecting device such as an Ethernet device (not shown) for reading instructions and/or data from a computer-readable medium, such as a floppy disk, a CD-ROM, a DVD, a MOD or an other digital source such as a network or the Internet, as well as yet to be developed digital means. In another embodiment, the computer 22 executes instructions stored in firmware (not shown). Computer 22 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, or the like, or a combination comprising at least one of the foregoing computers.

In addition to the data processing functions listed above, computer 22 is configured to provide control signals and/or information to DAS 24 and x-ray controller 26, according to another embodiment. More particularly, the DAS 24 samples analog data from detector elements 21 and converts the data to digital signals for subsequent processing by computer 22. Thus, the data stream generated by the radiation detector 20 comprises analog data, whereas the data stream received by the computer 22 comprises digital data.

In one embodiment, certain data processing steps may be performed in the DAS 24 or in the computer 22, depending on the specific DAS 24 employed. For certain embodiments, such as the energy discriminating detector embodiment described below, DAS 24 is configured to generate at least two data sets from the analog data stream, each of the data sets being characterized by a respective energy spectrum. For these embodiments, the digital data stream received by the computer 22 from DAS 24 comprises the data sets, and the computer 22 is configured to process the data sets to generate the multi-energy data set, such as multi-energy images. For other embodiments, computer 22 is configured to generate at least two data sets from the digital data stream received from the DAS 24, each of the data sets being characterized by a respective energy spectrum, and to process the data sets to generate the multi-energy data set, such as multi-energy images.

As noted above, the system enables a rapid inspection of cargo containers for a wide variety of materials in a wide variety of configurations and can used to accurately deduce the atomic number of high atomic elements. In one embodiment, the method may be used for dynamically quantifying the constituents of the article based on the material characterization images, wherein the step of dynamically quantifying the constituents comprises determining an amount of one of the constituents relative to another of the constituents. The system can be advantageously used to inspect airplane fuselages, carriages on semi-trailer tractors, trains or ships.

The invention is further illustrated by the following non-limiting examples.

EXAMPLE

This example was conducted to demonstrate how the aforementioned method can be used to effect the determination of the atomic number of hitherto unknown elements in an article.

Figure 3:
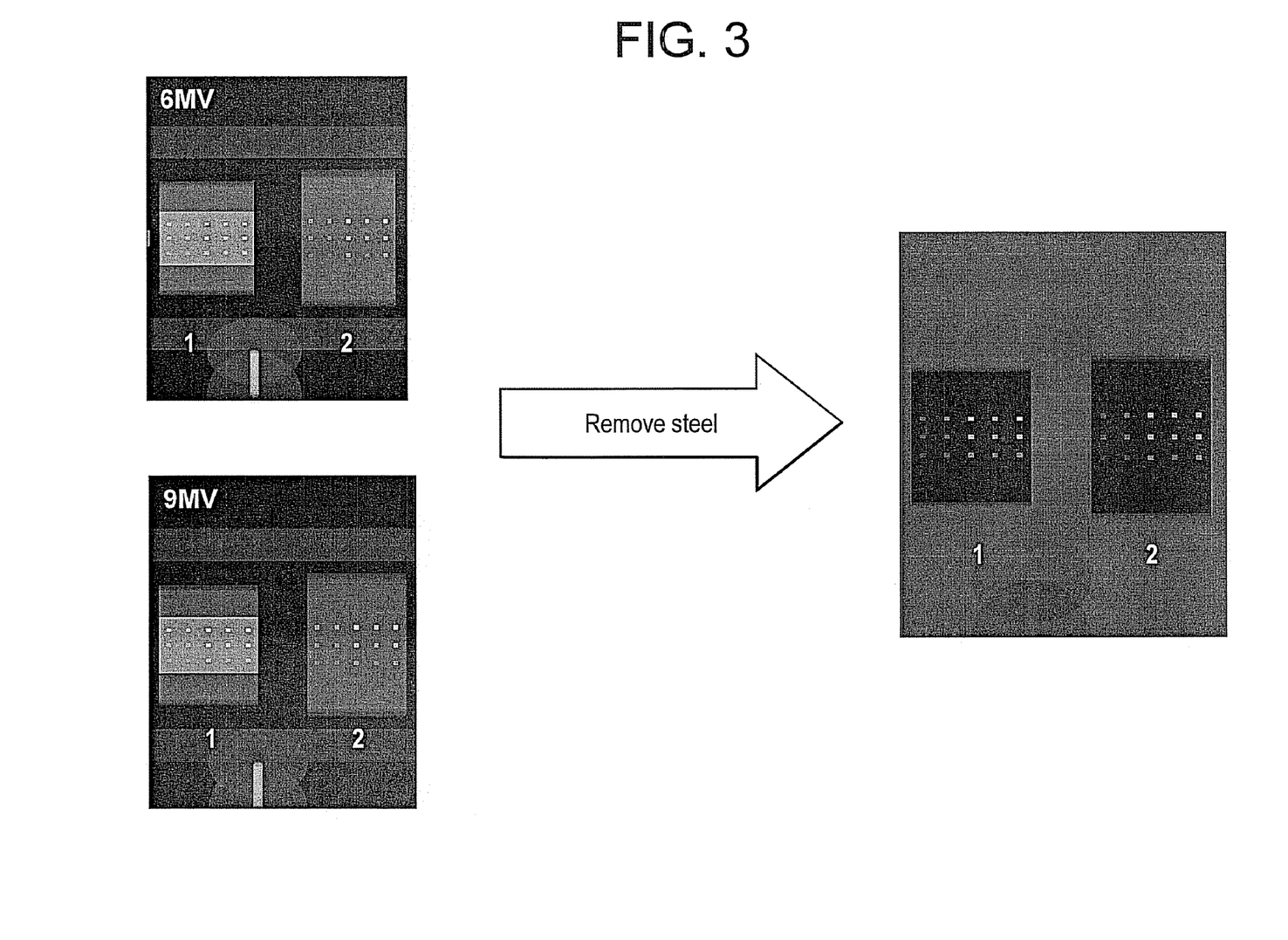
FIG. 3 depicts the combining of the low energy image with the high energy image (on the left of the arrow) and the filtering of the background to develop an image that contains regions of interest.

As shown in the FIG. 3, a cargo container containing 2 boxes of different materials were examined using x-radiation at two different energy levels. FIG. 3 shows a plan of the cargo container. The 2 boxes are titled Box #1 and Box #2 respectively. Each box contain 3 sets of materials as described below:

Box #1: Sets of materials comprising high atomic number elements (described below as Set #1, #2 and #3 respectively) were covered by a stack of paper, a slab of steel and a wood block. The stack of paper had a thickness of 1 meter. The slab of steel had dimensions of 1 meter in the horizontal direction and 0.6 meters in the vertical direction. The wood block had dimensions of 1 meter in the horizontal direction and 1.5 meters in the vertical direction. Thus the paper, slab of steel and wood block overlapped with the objects contained in Set #1, 2 and 3 described below:

Set #1 (first row from the bottom) comprised objects in order from left to right that comprise copper (Z=29), tin (Z=50), tungsten (Z=74), lead (Z=82) and uranium (Z=92). Each object had dimensions of 4.6 centimeter (cm)×4.6 cm when viewed from above. The thickness of each object was 4.6 cm.

Set #2 (second row from the bottom) comprised objects in order from left to right that comprise copper (Z=29), tin (Z=50), tungsten (Z=74), lead (Z=82) and uranium (Z=92). Each object had dimensions of 4.6 centimeter (cm)×4.6 cm when viewed from above. The thickness of each object was 10 cm.

Set #3 (third row from the bottom) comprised objects in order from left to right that comprise copper (Z=29), tin (Z=50), tungsten (Z=74), lead (Z=82), and uranium (Z=92). Each object had dimensions of 4.6 centimeter (cm)×4.6 cm when viewed from above. The thickness of each object was 15 cm.

Box #2 contained the same objects as in Set # 1, 2 and 3 with only an overlapping wood block wherein the wood block had dimensions of approximately 1 meter in the horizontal direction, 1.5 meters in the vertical direction and 1 meter along the scan direction (along the source and detector)

Figure 4:
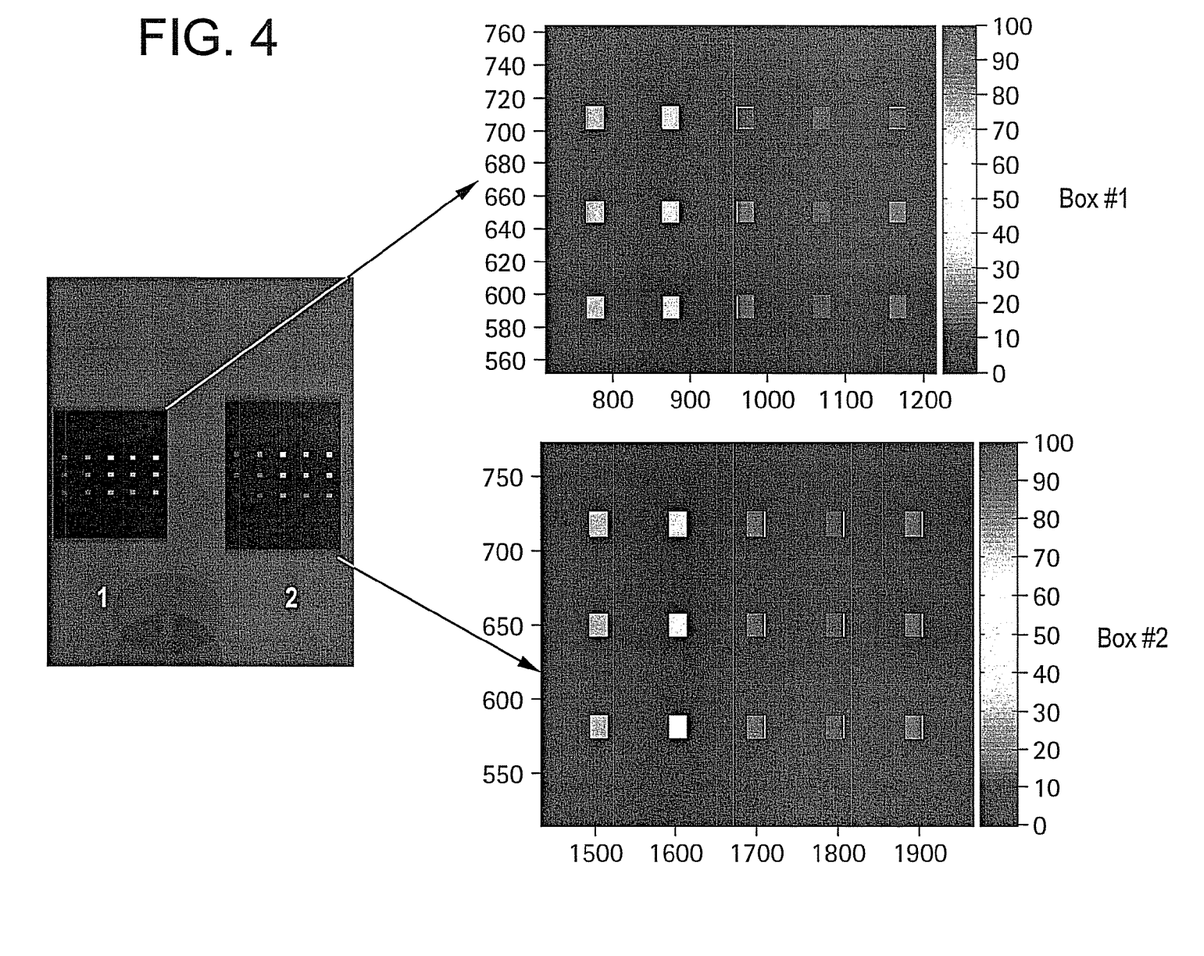
FIG. 4 depicts the regions of the cargo container that contain high atomic number elements.

The baseline was generated using a linear accelerator (linac) source with interlaced 6 and 9 megavolt (MV) emission capabilities and a source-to-detector-distance (SDD) of 9 meters. A vertical tower of detectors with a pixel size of 4 millimeters (mm) in height and 6 mm in width (4 mm×6 mm) was used to detect radiation on the side of the cargo container that was opposed to the side facing the linac source. FIGS. 3 and 4 are simulated without any noise.

The modeling was performed in several steps. The first step consisted of generating projection sets without quantum (x-ray) noise at linac (linear accelerator) voltages of 6 MV and 9 MV. The image sets were normalized by flat-field or air values and converted to opacity (attenuation length) values referred to as p-values.

In order to resolve the identity and the quantity of the high atomic number materials present in the cargo container, the low energy image at 6 MV is combined with the high energy image at 9 MV and the overlapping steel background is removed and used as a filter.

As noted above, once the contribution from the steel is removed, an image that depicts the materials having atomic numbers different from those of iron (the major constituent of steel) appear as hot spots. This is depicted in the FIG. 4, where images (on the left of the arrow having the description "remove steel") obtained at 6 MV and 9 MV were combined following the removal of the overlapping steel background to produce an image on the right. The image on the right contains regions of interest that can be further analyzed for high atomic number materials.

The FIG. 4 depicts how the Box #'s 1 and 2 that contain materials that comprise high atomic number elements are analyzed in those regions of interest to determine the presence of the high atomic number. As noted above, algorithms such as those described in the Equations (IV) and (V) above can be use in conjunction with a look-up table to determine the atomic numbers of elements in the regions of interest.

The aforementioned method can be used to detect high atomic number elements that can be used to cause undesirable destruction. It can also be used for the detection of high atomic number elements in medical imaging.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention.

What is claimed is:

1. A method for inspecting an article comprising a plurality of elements, wherein one element is selected as a background element, the method comprising:
    irradiating the article with radiation comprising a first energy and a second energy;
    receiving data that corresponds to the first energy and the second energy;
    processing the data to generate a first data set and a second data set; wherein the first data set corresponds to the first energy and wherein the second data set corresponds to the second energy;
    obtaining an attenuation ratio for the background element present in the article; the attenuation ratio for the background element being an attenuation in energy produced by the background element at the first energy to an attenuation in energy produced by the background element at the second energy;
    subtracting the attenuation ratio for the background element at the second energy from a product of the attenuation ratio for the background element with the first energy data set to form a filtered data set;
    identifying a region of interest in the filtered data set; and
    calculating an effective atomic number from the filtered data set for elements that have an atomic number greater than the background element in the region of interest.

2. The method of claim 1, wherein the second energy has a higher mean energy than the first energy.

3. The method of claim 1, wherein the irradiating the article with the first energy and the second energy can be conducted simultaneously or sequentially.

4. The method of claim 1, wherein the attenuation ratio is a p-value ratio R for a given element in the article is defined as shown in Equation (II) below:

$$R = \frac{P_{low}}{P_{high}} = a_{z_0} + a_{z_1}.P_{low} + a_{z_2}.P_{low}^2 + \ldots \quad (II)$$

where $P_{low}$ is the p-value at the lower energy of the first energy or the second energy; $P_{high}$ is the p-value at the higher of the first energy or the second energy, and where the polynomial coefficients $a_{z_0}$, $a_{z_1}$ and $a_{z_2}$ are dependent upon the atomic number Z, where the p-value is defined as shown in Equation (I)

$$P = -\log\left(\frac{I_{object}}{I_{air}}\right) \quad (I)$$

where $I_{object}$ is a measured energy with the article at a given pixel or a given collection of pixels, while $I_{air}$ is a measured energy without the article measured at the at the same pixel or given collection of pixels.

5. The method of claim 1, wherein the first data set, the second data set, and the filtered data set are each used to produce a respective image.

6. The method of claim 1, further comprising dynamically quantifying the elements of the article based upon the respective data sets, wherein the dynamically quantifying the elements comprises determining an amount of one of the elements relative to another of the elements.

7. The method of claim 1, wherein the first energy and the second energy comprise energy distributions.

8. The method of claim 1, wherein the calculating the atomic number of elements that have an atomic number greater than the background element in the region of interest is accomplished by utilizing a mathematical algorithm.

9. The method of claim 1, wherein calculating an effective atomic number from the filtered data set for elements that have an atomic number greater than the background element in the region of interest comprises solving the Equations (IV) and (V) below:

$$d = c_{z0} + c_{z1} \cdot P_{low} + c_{z2} \cdot P^2_{low} \quad (IV)$$

$$Z = b_{f0} + b_{f1} \cdot R + b_{f2} \cdot R^2 + \quad (V)$$

where d is the thickness, Z is the atomic number of the elements other than the background element and where the polynomial coefficients $c_{z0}$, $c_{z1}$, and $c_{z2}$, are dependent upon the atomic numbers of the elements other than the background element present in the article; and where the polynomial coefficients $b_{f0}$, $b_{f1}$, and $b_{f2}$, are dependent upon the element that constitutes the background; and where R is defined in the equation (II)

$$R = \frac{P_{low}}{P_{high}} = a_{z_0} + a_{z_1}.P_{low} + a_{z_2}.P_{low}^2 + \ldots \quad (II)$$

where $P_{low}$ is the p-value at the lower energy of the first energy or the second energy; $P_{high}$ is the p-value at the higher of the first energy or the second energy, and where the polynomial coefficients $a_{z_0}$, $a_{z_1}$ and $a_{z_2}$ are dependent upon the atomic number Z.

10. The method of claim 1, wherein calculating an effective atomic number from the filtered data set for elements that have an atomic number greater than the background element in the region of interest comprises using curve fitting.

11. The method of claim 1, wherein calculating an effective atomic number from the filtered data set for elements that have an atomic number greater than the background element in the region of interest comprises using a data table.

12. The method of claim 9, further comprising using curve fitting and/or using a data table to estimate the atomic number Z of the remaining elements present in the article.

13. A radiography system for implementing the method of claim 1.

\* \* \* \* \*

UNITED STATES PATENT AND TRADEMARK OFFICE
CERTIFICATE OF CORRECTION

PATENT NO. : 7,809,103 B2
APPLICATION NO. : 11/756027
DATED : October 5, 2010
INVENTOR(S) : Du et al.

Page 1 of 1

It is certified that error appears in the above-identified patent and that said Letters Patent is hereby corrected as shown below:

In Fig. 1, Sheet 1 of 4, delete " 2    2 " and insert -- 2    4 --, therefor.

In Column 1, Line 52, delete "91 MV," and insert -- 9 MV, --, therefor.

In Column 2, Line 44, delete "forms" and insert -- forms "a", --, therefor.

In Column 6, Line 1, in Equation (V), delete " $Z=b_{f0}+b_{f1}\cdot R+b_{f2}\cdot R^2+$ " and insert -- $Z=b_{f0}+b_{f1}\cdot R+b_{f2}\cdot R^2+\cdots$ --, therefor.

In Column 6, Line 7, delete "(N)" and insert -- (IV) --, therefor.

In Column 6, Line 19, delete "(N)" and insert -- (IV) --, therefor.

In Column 6, Line 24, delete "(N)" and insert -- (IV) --, therefor.

In Column 12, Line 6, in Claim 9, in Equation (V), delete " $Z=b_{f0}+b_{f1}\cdot R+b_{f2}\cdot R^2+$ " and insert -- $Z=b_{f0}+b_{f1}\cdot R+b_{f2}\cdot R^2+\cdots$ --, therefor.

Signed and Sealed this
Eighteenth Day of October, 2011

David J. Kappos
*Director of the United States Patent and Trademark Office*